United States Patent [19]
Lucovsky et al.

[11] Patent Number: 5,828,460
[45] Date of Patent: Oct. 27, 1998

[54] APPARATUS FOR OPTICAL INSPECTION OF METALLIC SURFACES

[75] Inventors: Arcady Lucovsky, Hod Ha-Sharon; Arcady Gershanik, Beer-Sheva; Leonid Lipetsker, Arad, all of Israel

[73] Assignee: S.Q.C.C. Ltd., Industrial Zone Raanana, Israel

[21] Appl. No.: 500,495

[22] Filed: Jul. 11, 1995

[51] Int. Cl.[6] .................................................. G01N 21/47
[52] U.S. Cl. .............................. 356/446; 356/73; 250/301
[58] Field of Search .................................... 356/417, 446, 356/371, 70, 73, 318; 250/301, 341.8, 461.1

[56] References Cited

U.S. PATENT DOCUMENTS

| 138,102 | 6/1873 | Torao et al. | 356/318 |
| 4,265,535 | 5/1981 | Pitt | 356/70 |
| 4,479,714 | 10/1984 | Lehrer | 356/345 |
| 5,040,889 | 8/1991 | Keane | 356/51 |
| 5,282,017 | 1/1994 | Kasindorf | 356/446 |
| 5,377,000 | 12/1994 | Berends | 356/73 |

FOREIGN PATENT DOCUMENTS 256440  11/1969  Russian Federation .
1393057  2/1982  Russian Federation .

OTHER PUBLICATIONS

ISO 8501–1: 1988—Visual assessment of surface cleanliness (no month availability).

Primary Examiner—Frank G. Font
Assistant Examiner—Zandra V. Smith
Attorney, Agent, or Firm—Wigman, Cohen, Leitner & Myers, P.C.

[57] ABSTRACT

An apparatus and method for inspection of metallic surfaces before subsequent treatment thereof (for example, painting) are disclosed. In accordance with the invention, several light sources illuminate the inspected surface with light beams having different wave lengths, reflected radiation is detected and converted to electrical signals, the electrical signals are processed digitally, and the results of processing are displayed. Some of the light sources are mounted so as to produce light beams inclined with respect to the inspected surface. These light beams are defined by an angular divergence of not more than 5 degrees. Display of results can be presented, in terms of the ISO standard, for inspection and assessment of industrial steel surfaces (i.e., in terms of preparation grades).

22 Claims, 4 Drawing Sheets

APPARATUS FOR OPTICAL INSPECTION OF METALLIC SURFACES

FIELD OF THE INVENTION

The present invention relates to the field of technological quality control, and more particularly, to the inspection of steel surfaces before or during preparation thereof for painting or other surface treatment steps.

Surface preparation here means cleaning of the surface from rust, mill scale, oil, grease and/or other contaminants. This step is an essential part of different technological processes, such as anticorrosive protection, welding, soldering, etc.

Preparation of metallic, in particular, steel, surfaces is associated with imparting of certain roughness, which may influence the quality of coating if the roughness is excessive or insufficient. On the other hand, excessive or insufficient cleaning, for example, by shot blasting, is associated with superfluous consumption of materials and labour expenditure. Therefore, inspection enabling correct assessment of the surface condition in terms of its cleanliness and roughness is a sufficient precondition which should be met in order to prepare the surface in a most efficient and economical way and to ensure the achieving of reliable and durable coatings.

BACKGROUND OF THE INVENTION

For the inspection and assessment of industrial steel surfaces, the ISO Standard 8501, qualitatively specifies the cleanliness of steel surfaces in terms of grades designated as Preparation Grades. In the form of pictures this standard classifies said Preparation Grades depending on the amount of rust and mill scale, which remains on the surface, after the cleaning process.

Furthermore, the ISO Standard 8501 also defines said Preparation Grades with respect to the type of cleaning technology to be chosen (e.g., shot blasting, power tool cleaning, flame cleaning, etc.) and with respect to the initial condition of the surface before cleaning, which is designated as Rust Grade.

Besides Preparation Grades and Rust Grades the above standard also specifies requirements of the inspected surface with regard to the absence of oil contaminant thereon over a particular threshold limit.

The main difficulty associated with implementation of the above standard in practice lies in the fact that attribution of the inspected surface to certain Preparation Grade and Rust Grade, as well as excessive oil presence has to determine by visual assessment whether the surface in question is identical or not to a particular picture, corresponding to a particular grade. It can be readily appreciated, that this method suffers from subjectivity and cannot be considered as suitable for reproducible industrial quality control.

Also known are some attempts to make the attribution procedure independent of subjectivity, but inevitably associated with visual assessment by the naked human eye.

For example, there is a known method and an optical device for determination of amount of rust on the surface of a metallic tube after its cleaning, as disclosed in SU 256440.

In accordance with this method the inspected surface is illuminated by a visual light beam so as to receive a reflected light beam. The intensity of the reflected beam is measured by means of a photo sensor in terms of current, and this value is used for calculation of the amount of rust by an empirical formula. The formula has been developed by empirical study of the correlation between intensity of reflected light exhibited by steel surfaces with the known amount of rust, determined beforehand by chemical analysis.

The disadvantage of this method and device for implementation thereof is associated with the fact that the above empirical relationship is valid only for those surfaces which were taken as standard without, however, the possibility of linking this relationship with Rust Grades, as designated in the above mentioned ISO standard, since the amount of rust is not taken into consideration.

Furthermore, the above method does not enable unequivocal selection of surfaces coated by red rust (hematite) from those coated by black rust (magnetite) or unrusted surfaces.

It should be emphasized, that the above method and device is suitable only for arbitrary attribution of steel surfaces depending on the amount of rust present thereon and is incapable of attributing the surface by amount of oil contaminants, preparation grade and surface roughness.

Another known device for determination of cleanliness of a metallic surface, is as disclosed in SU 1393057. This device consists of an infrared light source, an elliptic light collector, and a photo sensor. The device measures the intensity of diffusive radiation obtained after illumination of the inspected surface by IR light waves. The assessment of the inspected surface by means of this device is based on the assumption of proportionality between diffusive radiation and purity level of the metal surface under inspection.

The disadvantage of this approach lies in the fact that it does not take into consideration different influencing factors that destroy said proportionality. Among them are the strong influence of roughness, caused by such preparation methods like shot blasting or scraping used for highly rusted surfaces, the effect of excessive oil presence, etc. Furthermore, measurement of IR diffusive radiation intensity does not allow for selection of rust grade depending on whether two or three valent iron ion is present in the rust or whether the surface is clean of rust. The known device is merely suitable for providing the customer with the value of radiation intensity but without giving the surface attributions as to certain preparation grade, detection of presence of oil, or measurement of roughness.

In conclusion it should be stated that despite the known methods and devices for optical inspection of metallic surfaces which enable separate detection of contaminants thereon or measuring roughness thereof, there is no known universal device which enables simultaneous assessment and attribution of the inspected surface as to certain rust grade and/or preparation grade and/or oil contaminants presence and/or to surface roughness quality.

OBJECT OF THE INVENTION

The object of the present invention is to provide a device for optical inspection of metallic, in particular, steel, surfaces in which the above mentioned drawbacks of known devices are sufficiently reduced or overcome, however without losing their inherent benefits.

In particular, the first object of the present invention is to provide a new and universal device for optical inspection of steel surfaces which enables simultaneous detection of rust and/or oil contaminants on the inspected surface as well measuring of roughness of the surface with subsequent automatic attribution of the inspected surface to a certain rust and/or preparation grade.

Another object of the present invention is to provide a new, simple, compact and convenient inspection device suitable for manual operation by an operator.

Still a further object of the present invention is to provide an improved optical inspection device which ensures reproducible automatic attribution of the inspected surface to a certain grade.

Another object of the present invention is to provide for a new, simple and versatile optical inspection device suitable not only for detection of contaminants and attribution of the inspected surface to a certain grade but also for displaying results of inspection in terms of ISO standards, including rust and/or preparation grade and/or oil contamination presence and/or surface roughness.

The above and other objects and advantages of the present invention can be achieved in accordance with the following combination of its essential features, referring to different embodiments thereof.

An apparatus for optical inspection of metallic, in particular, steel, surfaces, said apparatus comprising a housing, provided with a window, enabling viewing therethrough of said inspected surface,
characterized in that said apparatus comprises
  a plurality of light sources, enabling illumination of the inspected surface via said window, wherein the inner surface of said housing is capable of reflecting total radiation, caused by said inspected surface after it has been illuminated by at least one of said sources;
  a detection means, comprising at least one photo responsive cell, enabling detecting of radiation, reflected by said inner surface of said housing and generating of corresponding electrical signals thereupon;
  a control means, enabling operating of said light sources and digital treatment of said electrical signals;
  a display means, showing thereupon said digital treatment results of inspection of said inspected surface in terms of presence of oil and/or cleanliness grade (rust grade, preparation grade) and/or roughness.

In accordance with one of the preferred embodiments said plurality of light sources comprises
  a first light source, enabling illumination of the inspected surface via said window by a light beam, having wave length in UV region
  a second light source, enabling illumination of the inspected surface via said window by a visible light beam, having a wave length of less than 500 nm;
  at least two additional light sources, enabling illumination of the inspected surface via said window by a light beams, having a wave length of more than 550 nm.

In accordance with another embodiment, said second light source and said additional light sources are formed as sources, producing collimated light beams, wherein said beams are defined by their angular divergence of not more than 5 degrees, and said beams also not being parallel.

In a third preferred embodiment, at least one of said light sources is mounted within said housing with the possibility of varying direction of the light beam, produced thereby.

As per still another preferred embodiment, said second light source is mounted within said housing so as to direct the light beam produced thereby with respect to said inspected surface at an angle of 60–70 degrees;
  at least one of said additional light sources is mounted within said housing in close proximity to said inspected surface so as to direct the light beam, produced thereby with respect to said inspected surface at an angle of not more than 12 degrees;
  and the second of said additional light sources is mounted within said housing remote with respect to said inspected surface so as to direct the light beam, produced thereby with respect to said inspected surface at an angle of 60–70 degrees.

According to yet another preferred embodiment. The inner surface of said housing is provided with a region capable of absorbing part of the specular component of said total radiation.

In still a further preferred embodiment, said apparatus is formed with a handle to be gripped by an operator, said apparatus being provided with frontal and rear extremities, wherein the frontal extremity thereof is brought close to the inspected surface so as to enable viewing thereof through said window; the rear extremity thereof faces an operator and said display means is situated thereon.

In another preferred embodiment the inspection results are presented by said display means in terms of ISO standard. The present invention in its various embodiments has only been summarized briefly.

For a better understanding of the present invention as well of its advantages, reference will now be made to the following description of its embodiments taken in combination with accompanying drawings.

THE INVENTION DESCRIPTION

Figures 1, 2:
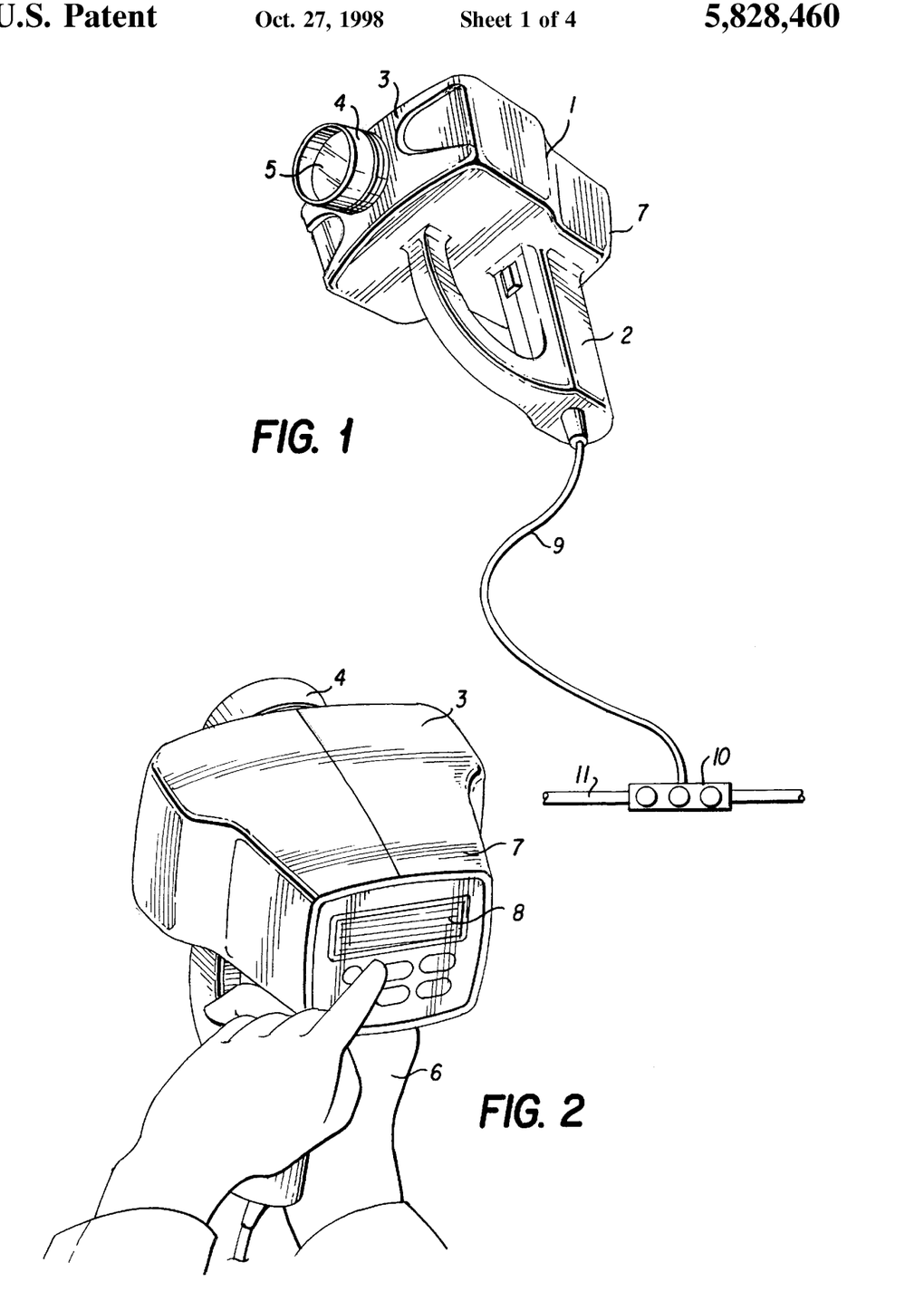
FIG. 1 shows the general isometrical view of the apparatus in accordance with the present invention as seen from the front side.
FIG. 2 shows the apparatus gripped by the operator's hand as seen from the rear side.
Figure 3:
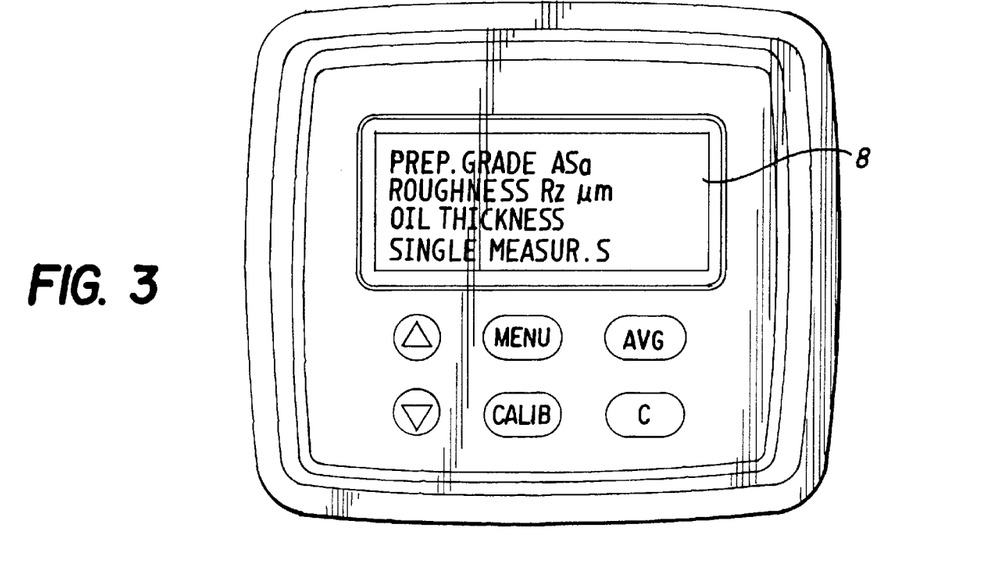
FIG. 3 is an enlarged view of the display means implemented in the apparatus in accordance with the present invention.

With reference to FIGS. 1,2,3 the apparatus for optical inspection of steel surfaces comprises the main body portion 1, provided with a handle 2 to be gripped by the operator's hand. At the frontal extremity 3 of the main body portion a cylindrical housing 4 is mounted and provided with a window 5. In the inspection mode the handle 2 is gripped in the operator's hand 6 and the apparatus is brought close to the inspected surface so as to enable viewing thereof through the window. The rear extremity 7 of the main body portion is provided with a screen 8 for displaying results of the inspection and with different knobs, enabling operation of the apparatus. In FIG. 3 shows an example of inspection results. In accordance with these results the inspected surface is attributed to ISO preparation grade ASa.

One can also see that the value of surface roughness in terms of Rz as well as oil thickness can be viewed on the screen.

In one of the preferred embodiments as shown in FIG. 1 the main body portion communicates via wiring 9 with an external source of energy, e.g. a replaceable pack of dry or rechargeable batteries 10. In the embodiment shown in FIG. 1 the source of energy is formed as an external autonomous unit, attachable to a belt 11 to be worn by an operator. By virtue of this provision the apparatus becomes portable and can be easily manually operated. It should be readily appreciated that the source of energy can also be formed as a dedicated built-in unit or as a net AC/DC power supply.

Figure 4:
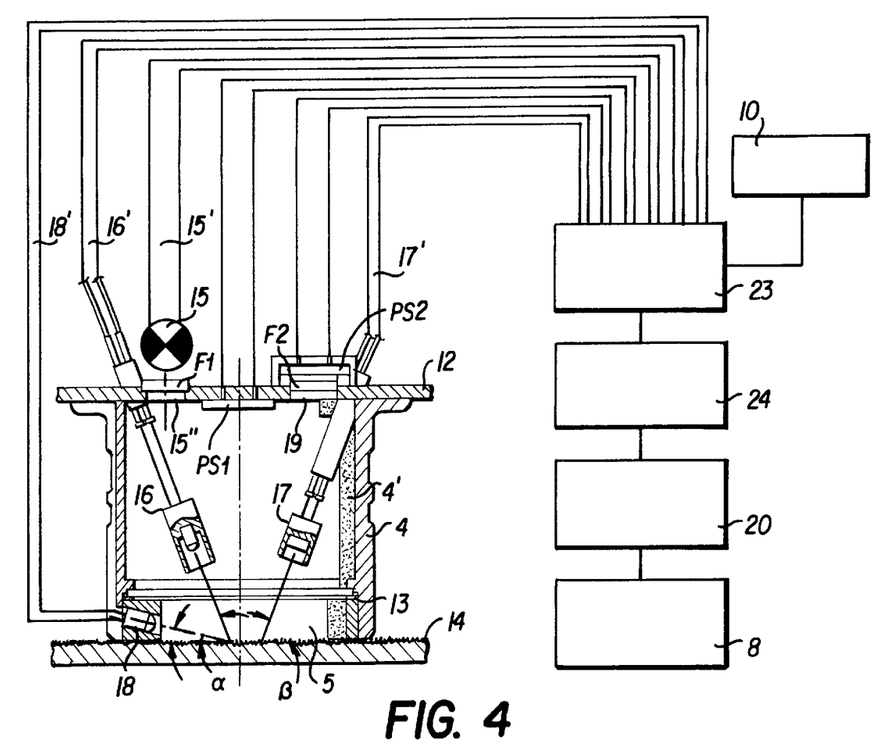
FIG. 4 schematically shows the apparatus in accordance with one of the preferred embodiments, including a block diagram with different components thereof.
Figure 5:
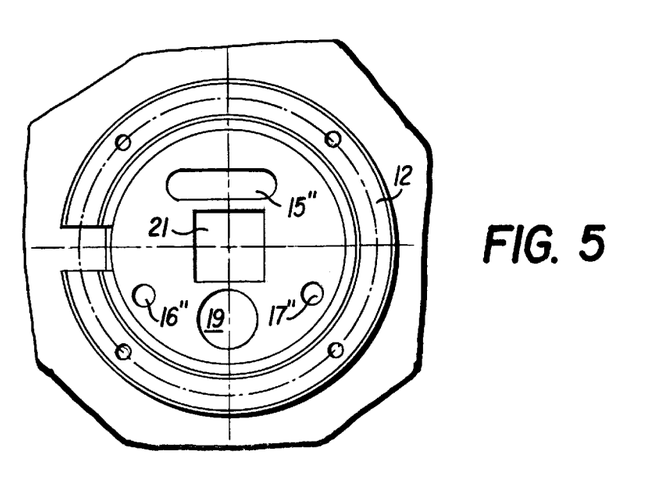
FIG. 5 presents a view of the housing employed in the apparatus as seen from the bottom part thereof.

With reference to FIGS. 4,5 construction of the housing as well of other components of the apparatus, mounted within the main body portion 1, will now be explained.

The housing 4 is formed as a cylindrical case and its rear part, situated adjacent to the main body portion is closed by an upper cover 12. The opposite part of the housing is provided with a window, covered by cover 13, situated within a case at a certain distance from the foremost extremity thereof. This cover is made of a material, for example, glass, which is translucent to UV, visible and IR radiation. By virtue of this provision the inspected surface 14 can be easily viewed through the window without any danger of breaking the cover when the foremost extremity of the housing is brought in contact with the inspected surface, as shown in FIG. 4.

In accordance with the present invention the main body portion and the housing are provided with a plurality of light sources, enabling illumination of the inspected surface by light beams, having different wave lengths. These light sources include a first light source 15, capable of radiating UV light, a second light source 16, capable of radiating visible light with short wave length not more than 500 nm and at least two additional light sources 17,18, capable of radiating light with long wave length of more than 550 nm, preferably IR light.

In practice it is recommended, that the above light sources employed in the apparatus in accordance with the present invention will be collimated light sources, capable of producing light beams with an angular divergence not exceeding 5 degrees.

It has also been empirically established that, in accordance with the present invention, location of the second light source 16 and both additional light sources 17, 18 should be chosen so as to satisfy certain requirements as follows.

The second light source should be situated within the housing remotely with respect to the surface 14 being inspected and the light beam, produced thereby should be slanted with respect to this surface at an angle of $\alpha=60-70$ degrees (see FIG. 4).

The additional light source 18 should be situated between the cover 13 and the inspected surface 14 so as to be in close proximity thereto. This light source should be slanted so as to produce a light beam, directed with respect to the inspected surface at an angle $\phi$, which is not more than 12 degrees.

The other additional light source 17 should be situated remotely with respect to the surface being inspected and the light beam, produced by this source should be slanted with respect thereto at an angle $\beta=60-70$ degrees. This beam should be inclined in an opposite sense with respect to the direction of light beam, produced by the second source 16.

It is schematically shown in FIG. 4 that all the above mentioned sources 15,16,17,18 are energized via respective wirings 15',16',17',18' by means of the above mentioned source of energy 10. Programmed operation of light sources is enabled by means of a controller 20, the functioning of which will be explained later on.

In the cover 12 there are formed openings which enable the connection of light sources 16, 17 with respective wirings 16',17'.

The cover is also provided with an opening 15", in which there is situated a filter means F1 which enables passage of UV light only. This light is produced by source 15 for illumination of inspected surface 14. An additional opening 19 is formed within the cover, and this opening is provided with a filter means F2. Mounted within openings 15", 19 respective filters F1,F2 are provided for retention of long waves, with lengths of more than 400 nm and for retention of short waves, with lengths less than 420 nm.

When the surface 14 is illuminated by at least one of the above light sources, total back radiation, consisting of diffusive and specular components, is effected. This back radiation is returned to the housing via window 5 and translucent cover 13. The major part of the inner wall of the housing is provided with a surface which enables reflecting of this back radiation and directing it to the upper cover 12, where it is detected by one of two photo sensors PS1,PS2, situated on the cover. The minor part of the inner wall is not provided with a reflecting surface, but constitutes a region, coated with a strip 4' made of light absorbing material. The significance of this provision will be explained further.

Upon illumination of the inspected surface by the above light sources, the electrical signals are generated by photo sensors, which are corresponding to intensity of back radiation. These signals are transmitted via respective wirings 21',22' to amplifier 23 and then to converter 24, which converts them to digital form.

Upon conversion these signals are transmitted to microprocessor/controller unit 20, where they are digitally treated according to a preprogrammed algorithm, enabling calculation of several quantitative parameters, corresponding to the condition of the inspected surface and simultaneous attribution of the inspected surface to certain roughness and/or preparation grade, preferably in terms of ISO Standard 8501.

In accordance with the present invention it has been found, that the intensity of back radiation, caused by each of the above sources can be used for qualitative and quantitative assessment of all the above mentioned parameters, required for attributing a certain cleanliness grade and roughness value to the inspected surface. In particular the first light source refers to detection of presence of oil and measuring of oil film thickness.

The second light source is relevant to detection of rust presence and type of rust. Two additional sources are employed for measuring of surface roughness.

It should be emphasized, that by virtue of the above constructional features of the apparatus in accordance with the present invention the functioning of the plurality of separate light sources, employed therein is not independent in the sense that intensities of back radiation caused by these sources become interrelated and can be used for correction of independent assessment parameters, thus improving reliability and versatility of attribution. These parameters refer to the presence and type of rust, the presence of oil contaminants and surface roughness and they are displayed on screen 8 together with the grade type. The algorithm, which enables calculation and correction of these parameters upon individual intensities of the back radiation caused by the above light sources, is omitted here for the sake of brevity.

Figure 6:
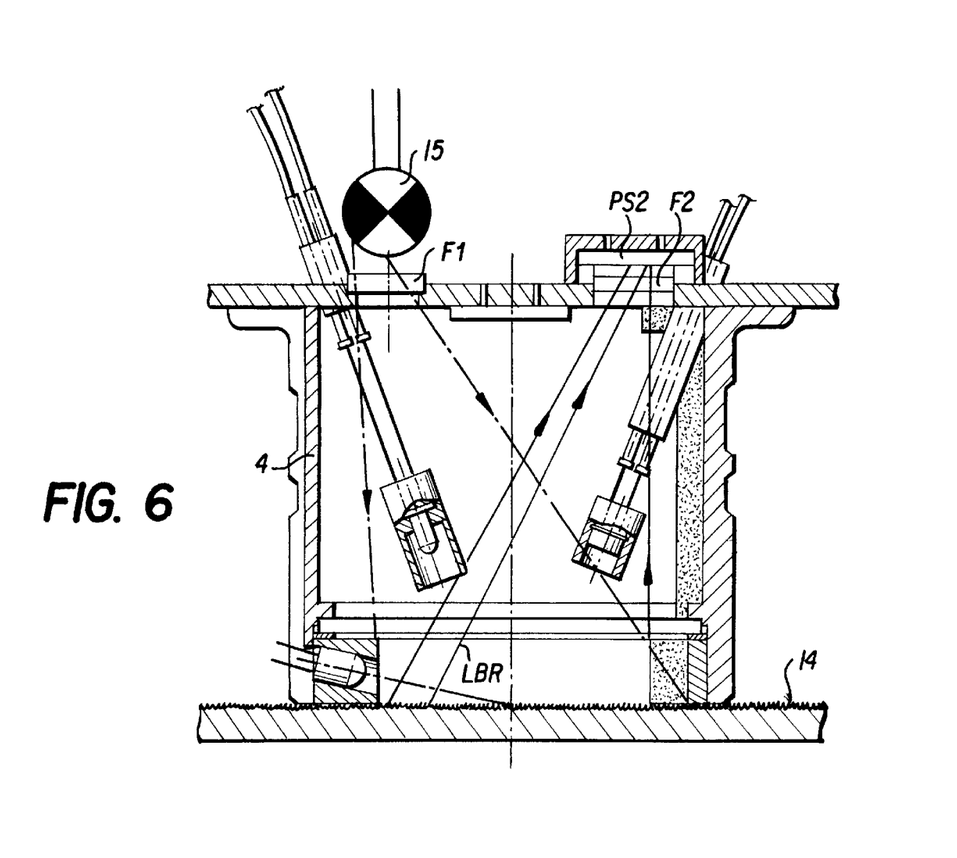
FIGS. 6–8 schematically explain the functioning of the apparatus.
Figure 7:
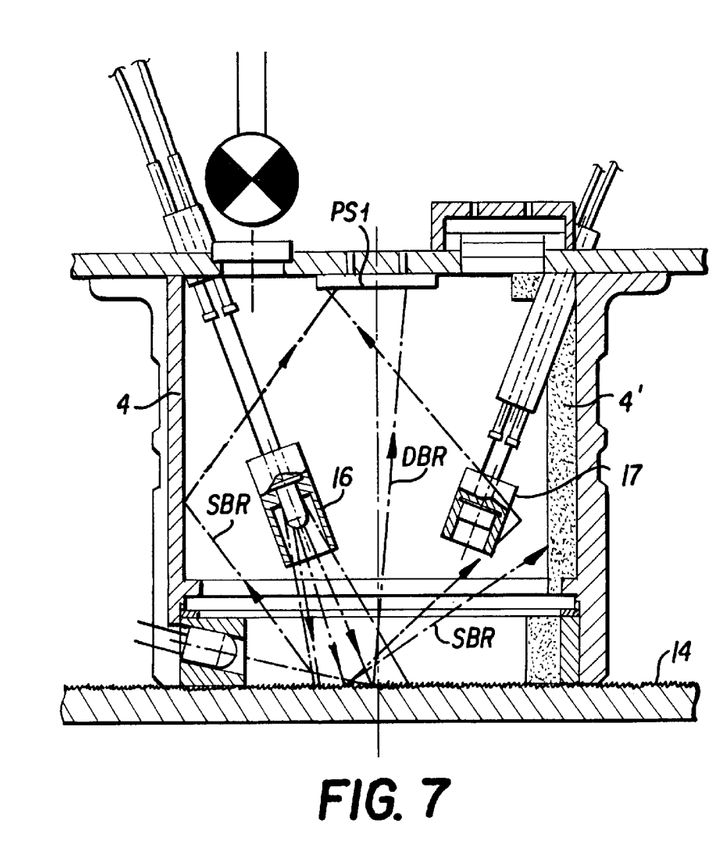
Figure 8:
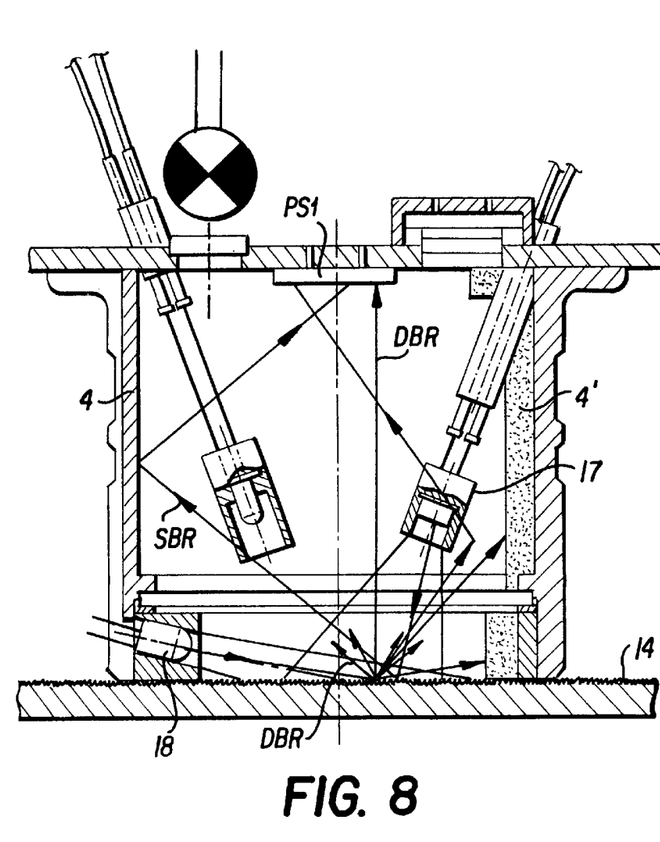

Having described, in general, the concept underlying the apparatus in accordance with the present invention, how this concept is implemented in practice will now be explained in more detail with reference to FIGS. 6–8.

In accordance with the sequence of events prescribed by the algorithm the first light source 15 is energized and illuminates the inspected surface 14 by UV light passing through filter F1. The illuminating light consists of light waves with lengths less than 400 nm, preferably 355–365 nm. The presence of grease/oil contaminants on the surface 14 will cause luminescent back radiation LBR. Said luminescent back radiation will be associated with light waves, having lengths more than 420 nm and their intensity will be measured by photo sensor PS2 after filtration from exciting UV-rays by filter F2. If the measured intensity of the luminescent back radiation exceeds some programmable threshold value, then the further sequence of events is interrupted and results in terms of an excessive amount of oil will be displayed on the screen.

In the case of a tolerable intensity of luminescence back radiation the UV-source 15 is de-energized, and the control unit will energize the second light source 16. This light source illuminates the inspected surface 14 by visible light with short waves having lengths less than 500 nm, for example blue light (see FIG. 7).

The light beam, produced by the second source 16 reaches the inspected surface and causes back radiation being collected by reflecting mirror walls of housing 4. This back radiation is detected by photo sensor PS1 and its intensity will be measured.

The incidental light beam, produced by the second light source 16 causes total back radiation, which consists of specular back radiation component SBR, directed by the surface 14 being inspected to the mirror walls of the housing and of diffused back radiation component DBR. In accordance with the present invention it has been found, that for correct measurement of intensity, associated with total back radiation and unequivocal attribution of the inspected surface thereupon one should ensure that intensity, associated with the diffused back radiation be approximately equal to that associated with the specular back radiation. By virtue of the inclination of the second light source at the above mentioned angle α, a certain part of the specular back radiation component SBR is directed towards the absorbing strip 4' so as to be absorbed thereby. It is not shown in detail, but should be understood, that this light source can be mounted within a housing with the possibility of varying this inclination angle by a dedicated conventional means (not shown).

Due to this provision the intensity of specular back radiation component SBR is partly reduced, and thus, the above requirement is satisfied. The particular configuration, dimensions and location of the light absorbing strip can be established empirically so as to achieve most efficient absorption of the specular radiation component.

After measurement of back radiation intensity, associated with illumination by light source 16 the additional light sources 17,18 are consequently energized, and the intensity associated with the back radiation caused thereby is measured by photo sensor PS1.

These intensities are used for measuring surface roughness by the two angles method, which is known per se and according to which the surface roughness is calculated as a ratio between them.

It has been established in accordance with the present invention, that in order to improve reliability of the assessment of surface roughness, the intensity of diffusive back radiation component DBR associated with light source 18 and measured by photo sensor PS1 should be approximately equal to the intensity of the specular back radiation component SBR. By virtue of inclination of the light source 18 at an angle φ not exceeding 12 degrees, the light beam produced by this source and the corresponding back radiation component satisfy the above requirement. By virtue of this provision, the apparatus can be advantageously used for reliable determination of surface roughness of different surfaces, irrespective of preparation technology, including shot blasting.

Therefore, by virtue of the present invention the inspection apparatus is universal in the sense that it enables the simultaneous obtainment of all necessary data defining the inspected surface and attributes it in terms of particular rust grade and/or preparation grade and/or presence of oil contamination and/or surface roughness. This data in terms of ISO standard designations is displayed on screen 18.

It can be readily appreciated, that the above described apparatus has very simple construction and its operation is easy and convenient for an operator.

It should be understood, that the present invention should not be limited to the above embodiments.

It should be understood also that changes and modifications can be made by any ordinary skilled in the art without deviation from the scope of the invention.

For example, it may not be necessary that components, responsible for the treatment of electrical signals produced by photo sensors will reside in the same main body portion where the light sources are located. These components can reside in a separate location, remote from the inspected surface. Communication between these components and photo sensors can be effected either through wirings or cordless.

Instead of two additional light sources illuminating the inspected surface by a long light waves and employed for measurement of surface roughness, one can use three or even more light sources so as to improve reliability of measurement.

It would be advantageous if the third light source were situated with respect to the light source 18 in such a manner that the light beam produced by the third source is perpendicular to the light beam produced by source 18.

The scope of the present invention is defined in the appended claims.

The features disclosed in the foregoing description, in the following claims and/or in the accompanying drawings may, both separately and in any combination thereof, be material for realizing the invention in diverse forms thereof.

We claim:

1. An apparatus for optical inspection of a substantially metallic surface, said apparatus comprising:

a housing, provided with a window, enabling viewing therethrough of said inspected surface;

a plurality of light sources for illumination of said inspected surface via said window, wherein the inner wall of said housing is provided with a reflecting surface for reflecting of back radiation effected by said inspected surface upon illumination thereof;

detection means, comprising at least one photo responsive cell, for enabling detecting of back radiation and for generating of corresponding electrical signals thereupon;

control means for controlling operation of said light sources and for digital processing of said electrical signals; and display means for showing, upon said digital processing, results of inspection of said inspected surface;

wherein said plurality of light sources comprises:

a first light source for illuminating the inspected surface via said window by a light beam having a wave length in a UV region;

a second light source for illuminating the inspected surface via said window by a visible light beam having a wave length less than 500 nm and defined by an angular divergence of not more than 5 degrees; and at least two additional light sources for illuminating the inspected surface via said window by light beams having wave lengths more than 550 nm and defined by angular divergence of not more than 5 degrees.

2. An apparatus as defined in claim 1, wherein an inner surface of said housing is provided with at least one region capable of absorbing at least part of a specular component of said total back radiation.

3. The apparatus as defined in claim 1, wherein at least one of said light sources is mounted within said housing with means for varying the direction of the light beam produced by said at least one of said light sources.

4. An apparatus as defined in claim 3, wherein an inner surface of said housing is provided with a region capable of maximally absorbing a specular part of back radiation effected by said inspected surface upon illumination thereof.

5. The apparatus as defined in claim 1, wherein said second light source is mounted within said housing, and wherein the light beam produced by said second light source is at an angle of between about 60–70 degrees with respect to said inspected surface, and wherein:

one of said at least two additional light sources is mounted within said housing in close proximity to said inspected surface so as to direct the light beam produced thereby at an angle of not more that 12 degrees with respect to said inspected surface; and another of said at least two additional light sources is mounted within said housing remote with respect to said inspected surface so as to direct the light beam produced thereby at an angle of between about 60–70 degrees with respect to said inspected surface.

6. An apparatus for optical inspection of a substantially metallic surface, said apparatus comprising:

a housing, provided with a window, enabling viewing therethrough of said inspected surface;

a plurality of light sources for illumination of said inspected surface via said window, wherein the inner wall of said housing is provided with a reflecting surface for reflecting of back radiation effected by said inspected surface upon illumination thereof;

detection means, comprising at least one photo responsive cell, for enabling detecting of back radiation, and for generating corresponding electrical signals thereupon;

control means for controlling operation of said light sources and for digital processing of said electrical signals; and display means for showing, upon said digital processing, results of inspection of said inspected surface;

wherein said plurality of light sources comprises:

a first light source for illuminating the inspected surface via said window by a light beam having a wave length in a UV region;

a second light source for illuminating the inspected surface via said window by a visible light beam having a wave length less than 500 nm and defined by an angular divergence of not more than 5 degrees; and at least two additional light sources for illuminating the inspected surface via said window by light beams having wave lengths more than 550 nm and defined by an angular divergence of not more than 5 degrees;

wherein said second light source and said additional light sources are formed as sources producing collimated light beams, wherein said beams are defined by an angular divergence of not more than 5 degrees.

7. An apparatus as defined in claim 6, wherein at least one of said light sources is mounted within said housing with means for varying the direction of the light beam produced thereby.

8. An apparatus as defined in claim 6, wherein said second light source is mounted within said housing so as to direct the light beam produced thereby at an angle of 60–70 degrees with respect to said inspected surface;

wherein one of said additional light sources is mounted within said housing in close proximity to said inspected surface so as to incline the light beam produced thereby at an angle of not more than 12 degrees with respect to said inspected surface; and wherein a second of said additional light sources is mounted within said housing remote with respect to said inspected surface so as to incline the light beam produced thereby at an angle of 60–70 degrees with respect to said inspected surface.

9. A device for optically inspecting a metallic surface, comprising:

first light means for illuminating said surface to produce first back radiation;

second light means for illuminating said surface to produce second back radiation;

third light means for illuminating said surface to produce third back radiation; and means responsive to said first back radiation for detecting oil on said surface, and responsive to said second back radiation for detecting rust on said surface, and responsive to said third back radiation for measuring roughness of said surface, wherein said first light means comprises a UV light source, said second light means comprises a visible light source, and said third light means comprises an infra-red light source, and wherein said first, second and third light means are disposed within a housing of a size to be held with one hand.

10. A method for optically inspecting a metallic surface, comprising the steps of:

(a) providing a metal surface to be tested;

(b) illuminating said surface with at least one of UV light and visible light;

(c) illuminating said surface with two additional light beams; and (d) using a two-angle method to measure surface roughness.

11. The method according to claim 10, wherein said surface is illuminated with UV light, and step (b) further comprises measuring an intensity of back radiation resulting from the illuminating with UV light.

12. The method according to claim 11, wherein no further illumination is carried out in step (b) if the measured intensity exceeds a predetermined threshold.

13. The method according to claim 11, wherein illumination with UV light is stopped if the measured intensity does not exceed a predetermined threshold, and said surface is then illuminated with visible light.

14. An apparatus for optically inspecting a metallic surface, comprising:

first means for illuminating said surface with at least one of UV light and visible light;

second means for illuminating said surface with two additional light beams; and control means for controlling the first and second means to illuminate said surface sequentially with said at least one of UV light and visible light and said two additional light beams, respectively.

15. The apparatus according to claim 14, further comprising measuring means for measuring an intensity of back radiation resulting from the illumination of said surface.

16. The apparatus according to claim 15, wherein said control means stops further illumination if the measured intensity exceeds a predetermined threshold.

17. The apparatus according to claim 15, wherein said control means stops illumination with UV light if the measured intensity does not exceed a predetermined threshold, and then illuminates said surface with visible light.

18. The apparatus according to claim 14, wherein said control means comprises a computer.

19. The apparatus according to claim 14, wherein said computer processes illumination data resulting from illumination of said surface.

20. The apparatus according to claim 14, further comprising data processing means for processing illumination data resulting from illumination of said surface.

21. The apparatus according to claim 20, wherein said control means controls said second means to illuminate said surface with said two additional beams at different, respective angles of incidences to obtain respective illumination data, and said data processing means processes said respective illumination data in accordance with a two-angle technique to determine the roughness of said surface.

22. A method for optically inspecting a metallic surface, comprising the steps of:
(a) providing a metallic surface to be tested;
(b) illuminating said surface with a first light for detecting oil;
(c) illuminating said surface with a second light for detecting rust; and
(d) illuminating said surface with a third light for measuring surface roughness, said third light comprising an infra-red light.

* * * * *

UNITED STATES PATENT AND TRADEMARK OFFICE
CERTIFICATE OF CORRECTION

PATENT NO. : 5,828,460
DATED : October 27, 1998
INVENTOR(S) : Lucovsky et al.

It is certified that error appears in the above-indentified patent and that said Letters Patent is hereby corrected as shown below:

```
On the title page, item [54] and column 1, line 1,
    change "APPARATUS" to --APPARATUS AND METHOD--.
```

Signed and Sealed this

Twenty-third Day of November, 1999

Attest:

Q. TODD DICKINSON

Attesting Officer

Acting Commissioner of Patents and Trademarks